US009480743B2

(12) United States Patent
Danek-Bulius et al.

(10) Patent No.: US 9,480,743 B2
(45) Date of Patent: Nov. 1, 2016

(54) PHARMACEUTICAL FORMULATION COMPRISING A BIOPHARMACEUTICAL DRUG

(75) Inventors: Martina Danek-Bulius, Kundl (AT); Britta Deutel, Kundl (AT); Sabine Fürtinger, Kundle (AT); Bernt Pragl, Kundle (AT); Drago Kuzman, Menges (SI)

(73) Assignee: Hexal AG, Holzkirchen (DE)

( * ) Notice: Subject to any disclaimer, the term of this patent is extended or adjusted under 35 U.S.C. 154(b) by 110 days.

(21) Appl. No.: 13/995,556

(22) PCT Filed: Dec. 28, 2011

(86) PCT No.: PCT/EP2011/074181
§ 371 (c)(1),
(2), (4) Date: Aug. 14, 2013

(87) PCT Pub. No.: WO2012/089778
PCT Pub. Date: Jul. 5, 2012

(65) Prior Publication Data
US 2013/0336968 A1    Dec. 19, 2013

(30) Foreign Application Priority Data
Dec. 28, 2010   (EP) .................................. 10197122

(51) Int. Cl.
| A61K 39/395 | (2006.01) |
| C07K 16/24 | (2006.01) |
| A61K 9/00 | (2006.01) |
| A61K 9/19 | (2006.01) |

(52) U.S. Cl.
CPC ......... *A61K 39/3955* (2013.01); *A61K 9/0019* (2013.01); *A61K 39/39591* (2013.01); *C07K 16/241* (2013.01); *A61K 9/19* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| 5,223,409 | A | 6/1993 | Ladner et al. ............... 435/69.7 |
| 5,859,205 | A | 1/1999 | Adair et al. ............... 424/130.1 |
| 6,248,516 | B1 | 6/2001 | Winter et al. ................. 435/6 |
| 6,300,064 | B1 | 10/2001 | Knappik et al. ............ 435/69.1 |
| 6,309,663 | B1 * | 10/2001 | Patel et al. ................... 424/450 |
| 6,331,415 | B1 | 12/2001 | Cabilly et al. ............... 435/326 |
| 6,548,640 | B1 | 4/2003 | Winter ...................... 530/387.1 |
| 2003/0204862 | A1 | 10/2003 | Kuehn et al. .................. 800/10 |
| 2004/0033228 | A1 | 2/2004 | Krause et al. |
| 2004/0120952 | A1 * | 6/2004 | Knight et al. ............. 424/145.1 |
| 2008/0090753 | A1 | 4/2008 | Pohl et al. ........................ 514/3 |
| 2009/0226530 | A1 * | 9/2009 | Lassner et al. ............... 424/497 |

FOREIGN PATENT DOCUMENTS

| EP | 0544359 A2 | 6/1993 | |
| EP | 1297842 | 4/2003 | |
| EP | 1688432 | 8/2006 | |
| EP | 2159230 A1 | 3/2010 | |
| EP | 2471554 | 7/2012 | |
| WO | WO 97/39027 | 10/1997 | |
| WO | WO 03/041680 | 5/2003 | |
| WO | WO 2004/019861 | 3/2004 | |
| WO | WO 2004/039315 | 5/2004 | |
| WO | WO 2004/048517 | 6/2004 | |
| WO | WO 2004/096179 | 11/2004 | |
| WO | WO 2006/044908 | 4/2006 | |
| WO | WO 2006/083689 | 8/2006 | |
| WO | WO 2006/087205 | 8/2006 | |
| WO | WO-2006/087205 A1 | 8/2006 | |
| WO | WO 2006081587 A2 * | 8/2006 | ........... A61K 9/0019 |
| WO | WO 2006/112838 | 10/2008 | |
| WO | WO 2008/132439 | 11/2008 | |
| WO | WO 2009/155723 | 12/2009 | |
| WO | WO 2010/040988 | 4/2010 | |
| WO | WO 2012/089778 | 7/2012 | |

OTHER PUBLICATIONS

Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25.*
Gokarn YR, et al. Self-buffering antibody formulations. Journal of Pharmaceutical Sciences, vol. 97, No. 8, pp. 3051-3066 (2008).
Leibl H, et al. Separation of polysaccharide-specific human immunoglobulin G subclasses using a Protein A Superose column with a pH gradient elution system. Journal of Chromatography, vol. 639, pp. 51-56 (1993).
International Preliminary Report on Patentability issued on Jul. 2, 2013 for PCT/EP2011/074181, filed on Dec. 28, 2011, published as WO 2012/089778 on Jul. 5, 2012 [Inventor—Danek-Bulius; Applicant—Hexal AG] [15 pages].
International Search Report and Written Opinion issued on May 16, 2012 for PCT/EP2011/074181, filed on Dec. 28, 2011, published as WO 2012/089778 on Jul. 5, 2012 [Inventor—Danek-Bulius; Applicant—Hexal AG] [24 pages].
Pujara CP, et al. Effects of formulation variables on nasal epithelial cell integrity: Biochemical evaluations. Intl. J. Pharmaceut. vol. 114, pp. 197-203 (1995).
Communication issued May 30, 2014 for European Patent Application EP 11807947.4 filed on Dec. 28, 2011, published as EP 2658575 on Jul. 2, 2014 [Inventor—Martina Danek-Bulius; Applicant—Hexal AG] [12 pages].
Office Action issued on Aug. 4, 2015 for Chinese Patent Application No. 201180062372.1 filed on Dec. 28, 2011 and published as Chinese Patent Publication No. 103269718 on Aug. 28, 2013 (4 pages).

(Continued)

*Primary Examiner* — Brian J Gangle
*Assistant Examiner* — Andrea McCollum
(74) *Attorney, Agent, or Firm* — Ballard Spahr LLP

(57) ABSTRACT

The present invention is related to a pharmaceutical formulation comprising a biopharmaceutical drug, said composition further comprising at least one mono- or dicarboxylic acid with a backbone of 2-6 C-Atoms, or at least one salt thereof.

10 Claims, 6 Drawing Sheets

(56) References Cited

OTHER PUBLICATIONS

Figure 1A:
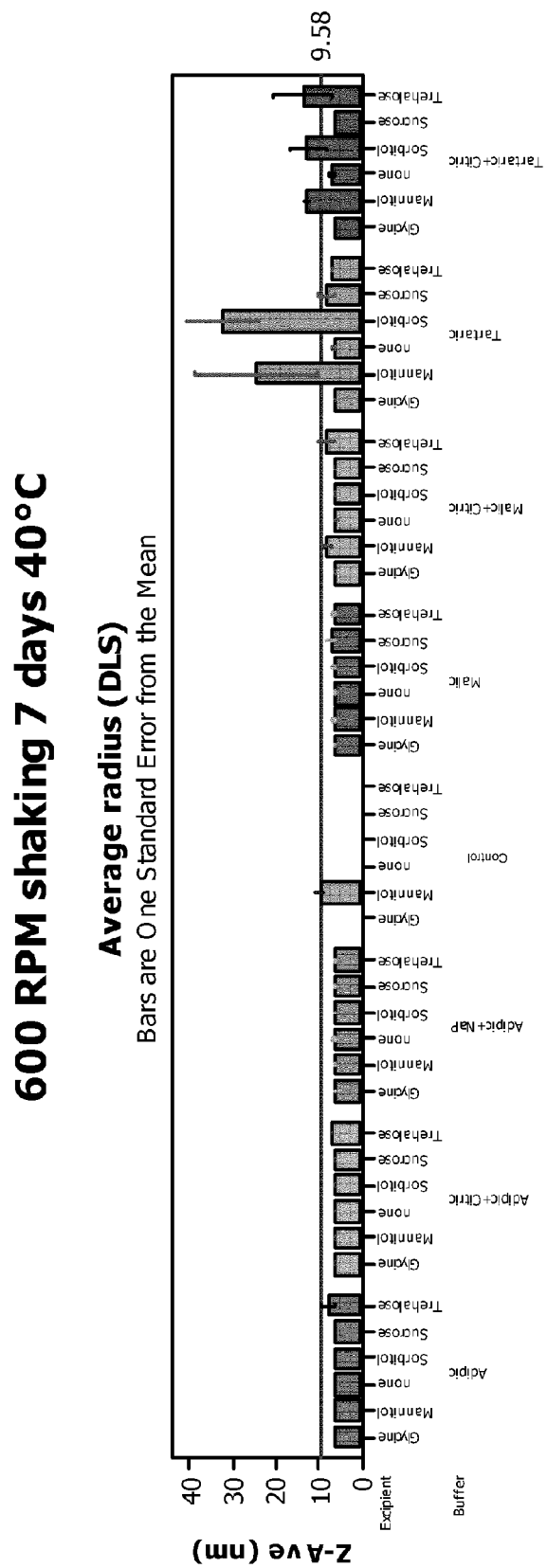

Office Action issued on Apr. 29, 2015 by the Federal Service for Intellectual Property of Russia for application RU 2013133953, filed on Dec. 28, 2011 (Applicant—Hexal AG // Inventor—Danek-Bulius, et al.) (Russian Original 4 pages // English Translation 3 pages).

Communication pursuant to Article 94(3) EPC issued on Apr. 5, 2016 for European Patent Application EP 11807947.4 filed on Dec. 28, 2011, published as EP 2658575 on Jul. 2, 2014 (Inventor—Martina Danek-Bulius; Applicant—Hexal AG) (9 pages).

Wang, et al., Instability, stabilization, and formulation of liquid protein pharmaceuticals, International Journal of Pharmaceutics, 185 (1999) pp. 129-188.

* cited by examiner

**Purity and Related substances by SE-HPLC –
Purity – in [Area-%] after 3 months storage**

**Sum of AP's – soluble aggregates detected by
SEC – in [Area-%] after 3 months storage**

SEQUENCE LISTING

<160> NUMBER OF SEQ ID NOS: 10

<210> SEQ ID NO 1
<211> LENGTH: 1413
<212> TYPE: DNA
<213> ORGANISM: Artificial
<220> FEATURE:
<223> OTHER INFORMATION: Anti TNFalpha IgG Heavy chain Coding sequence

<400> SEQUENCE: 1

```
atggcctggg tctggaccct gcctttcctg atggccgctg cccagtccgt gcaggccgag      60
gtgcagctgg tcgagtctgg cggcggactg gtgcagcctg ccggtccct gcggctgtcc      120 tgcgccgcct ccggcttcac cttcgacgac tacgccatgc actgggtccg ccaggccct     180 ggcaaaggcc tcgagtgggt gtccgccatc acctggaact ccggccacat cgactacgcc      240
gactccgtgg agggccggtt caccatctcc cggacaacg ccaagaactc cctgtacctg      300
cagatgaact ccctgcgggc cgaggacacc gccgtgtact actgcgccaa ggtgtcctac      360
ctgtccaccg cctcctccct ggactactgg ggccagggca cctggtcac cgtgtcctcc      420 gcctccacca agggcccctc cgtgttccct ctggcccctt cctccaagtc cacctccggc      480
ggcaccgccg ctctgggctg cctggtcaag gactacttcc ctgagcctgt gacagtgtcc      540
tggaactctg gcgccctgac cagcggcgtg cacaccttcc ctgccgtgct gcagtcctcc      600
ggcctgtact ccctgtcctc cgtcgtcaca gtgccttcct ccagcctggg cacccagacc      660
tacatctgca acgtgaacca caagccttcc aacaccaagg tggacaagaa ggtggagcct      720
aagtcctgcg acaagaccca cacctgccct ccctgccctg ccctgagct gctgggcgga      780 ccttccgtgt tcctgttccc tcctaagcct aaggacaccc tgatgatctc ccggaccct      840 gaggtcacct gcgtggtggt ggacgtgtcc cacgaggatc ctgaggtcaa gttcaattgg      900
tacgtggacg gcgtggaggt gcacaacgct aagaccaagc ctcgggaaga gcagtacaac      960
tccacctacc gggtggtgtc cgtgctgacc gtgctgcacc aggactggct gaacggcaaa     1020
gaatacaagt gcaaggtctc caacaaggcc ctgcctgccc ccatcgagaa aaccatctcc     1080
aaggccaagg gccagcctcg cgagcctcag gtgtacaccc tgcctccctc cgggacgag     1140 ctgaccaaga accaggtgtc cctgacctgt ctggtcaagg gcttctaccc ttccgatatc     1200
```

```
gccgtggagt gggagtccaa cggccagcct gagaacaact acaagaccac ccctcctgtg    1260
ctggactccg acggctcctt cttcctgtac tccaagctga ccgtggacaa gtcccggtgg    1320
cagcagggca acgtgttctc ctgctccgtg atgcacgagg ccctgcacaa ccactacacc    1380
cagaagtccc tgtccctgag ccctggcaag tga                                 1413
```

<210> SEQ ID NO 2
<211> LENGTH: 705
<212> TYPE: DNA
<213> ORGANISM: Artificial
<220> FEATURE:
<223> OTHER INFORMATION: Anti TNFalpha IgG Light chain Coding sequence

<400> SEQUENCE: 2

```
atgtccgtgc tgacccaggt gctggccctg ctgctgctgt ggctgaccgg caccagatgc     60
gacatccaga tgacccagtc ccctcctcc ctgtccgcct ccgtgggcga cagagtgacc     120
atcacctgcc gggcctccca gggcatccgg aactacctgg cctggtatca gcagaagcct    180
ggcaaggccc ctaagctgct gatctacgcc gcctccaccc tgcagtccgg cgtgccttcc    240
cggttctccg gctccggcag cggcaccgac ttcaccctga ccatctcctc cctgcagcct    300
gaggacgtgg ccacctacta ctgccagcgg tacaacagag ccccttacac cttcggccag    360
ggcaccaagg tggagatcaa gcgtacggtg gccgctcctt ccgtgttcat cttccctccc    420
tccgacgagc agctgaagtc cggcaccgcc agctcgtct gcctgctgaa caacttctac    480
cctcgggagg ccaaggtgca gtggaaggtg acaacgccc tgcagagcgg caactcccag    540
gaatccgtca ccgagcagga ctccaaggac agcacctact ccctgtccag cacccctgacc   600 ctgtccaagg ccgactacga gaagcacaag gtgtacgcct gcgaggtcac ccaccagggc    660
ctgtcctccc ccgtgaccaa gtccttcaac cggggcgagt gctga                    705
```

<210> SEQ ID NO 3
<211> LENGTH: 470
<212> TYPE: PRT
<213> ORGANISM: Artificial
<220> FEATURE:
<223> OTHER INFORMATION: Anti TNFalpha IgG Heavy chain amino acid
      sequence

<400> SEQUENCE: 3

```
Met Ala Trp Val Trp Thr Leu Pro Phe Leu Met Ala Ala Ala Gln Ser
1               5                   10                  15

Val Gln Ala Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140
```

```
Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 4
<211> LENGTH: 234
<212> TYPE: PRT
<213> ORGANISM: Artificial
<220> FEATURE:
<223> OTHER INFORMATION: Anti TNFalpha IgG Light chain amino acid
      sequence

<400> SEQUENCE: 4

Met Ser Val Leu Thr Gln Val Leu Ala Leu Leu Leu Leu Trp Leu Thr
1               5                   10                  15

Gly Thr Arg Cys Asp Ile Gln Met Thr Gln Ser Pro Ser Ser Leu Ser
```

```
                    20                  25                  30
Ala Ser Val Gly Asp Arg Val Thr Ile Thr Cys Arg Ala Ser Gln Gly
                35                  40                  45

Ile Arg Asn Tyr Leu Ala Trp Tyr Gln Gln Lys Pro Gly Lys Ala Pro
 50                  55                  60

Lys Leu Leu Ile Tyr Ala Ala Ser Thr Leu Gln Ser Gly Val Pro Ser
 65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Arg Tyr Asn
                100                 105                 110

Arg Ala Pro Tyr Thr Phe Gly Gln Gly Thr Lys Val Glu Ile Lys Arg
                115                 120                 125

Thr Val Ala Ala Pro Ser Val Phe Ile Phe Pro Pro Ser Asp Glu Gln
                130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
                210                 215                 220

Val Thr Lys Ser Phe Asn Arg Gly Glu Cys
225                 230

<210> SEQ ID NO 5
<211> LENGTH: 9
<212> TYPE: PRT
<213> ORGANISM: Artificial
<220> FEATURE:
<223> OTHER INFORMATION: Anti TNFalpha IgG Light chain CDR 3 amino acid
      sequence
<220> FEATURE:
<221> NAME/KEY: misc_feature
<222> LOCATION: (9)..(9)
<223> OTHER INFORMATION: Xaa can be any naturally occurring amino acid

<400> SEQUENCE: 5

Gln Arg Tyr Asn Arg Ala Pro Tyr Xaa
1               5

<210> SEQ ID NO 6
<211> LENGTH: 12
<212> TYPE: PRT
<213> ORGANISM: Artificial
<220> FEATURE:
<223> OTHER INFORMATION: Anti TNFalpha IgG Heavy chain CDR 3 amino acid
      sequence
<220> FEATURE:
<221> NAME/KEY: misc_feature
<222> LOCATION: (12)..(12)
<223> OTHER INFORMATION: Xaa can be any naturally occurring amino acid

<400> SEQUENCE: 6

Val Ser Tyr Leu Ser Thr Ala Ser Ser Leu Asp Xaa
1               5                   10

<210> SEQ ID NO 7
```

```
<211> LENGTH: 7
<212> TYPE: PRT
<213> ORGANISM: Artificial
<220> FEATURE:
<223> OTHER INFORMATION: Anti TNFalpha IgG Light chain CDR 2 amino acid
      sequence

<400> SEQUENCE: 7

Ala Ala Ser Thr Leu Gln Ser
1               5

<210> SEQ ID NO 8
<211> LENGTH: 17
<212> TYPE: PRT
<213> ORGANISM: Artificial
<220> FEATURE:
<223> OTHER INFORMATION: Anti TNFalpha IgG Heavy chain CDR 2 amino acid
      sequence

<400> SEQUENCE: 8

Ala Ile Thr Trp Asn Ser Gly His Ile Asp Tyr Ala Asp Ser Val Glu
1               5                   10                  15

Gly

<210> SEQ ID NO 9
<211> LENGTH: 11
<212> TYPE: PRT
<213> ORGANISM: Artificial
<220> FEATURE:
<223> OTHER INFORMATION: Anti TNFalpha IgG Light chain CDR 1 amino acid
      sequence

<400> SEQUENCE: 9

Arg Ala Ser Gln Gly Ile Arg Asn Tyr Leu Ala
1               5                   10

<210> SEQ ID NO 10
<211> LENGTH: 5
<212> TYPE: PRT
<213> ORGANISM: Artificial
<220> FEATURE:
<223> OTHER INFORMATION: Anti TNFalpha IgG Heavy chain CDR 1 amino acid
      sequence

<400> SEQUENCE: 10

Asp Tyr Ala Met His
1               5
```

PHARMACEUTICAL FORMULATION COMPRISING A BIOPHARMACEUTICAL DRUG

CROSS REFERENCE TO RELATED APPLICATIONS

The present application is a National Phase Application of International Application No. PCT/EP2011/074181, filed Dec. 28, 2011, which claims priority to European Patent Application No. 10197122.4, filed Dec. 28, 2010, which applications are incorporated herein fully by this reference.

SEQUENCE LISTING

Please direct entry of the attached "Sequence Listing" in the above-identified patent application. The enclosed text copy of the Sequence Listing serves as both a paper copy of the sequence listing under 37 C.F.R. 1.821(c) and a computer readable form under 37 C.F.R. 1.821(e). The sequence listing attached hereto an in compliance with 37 C.F.R. 1.821(c) and (e) is identical to the paper copy of the Sequence Listing which was submitted in PCT Application No. PCT/EP2011/074181, filed on Dec. 28, 2011, and includes no new matter, as required by 37 C.F.R. 1.821(e), 1.821(f), 1.821(g), 1.825(b), or 1.825(d). Therefore, entry of the Sequence Listing is respectfully requested.

The present invention is related to a pharmaceutical formulation comprising a biopharmaceutical drug.

INTRODUCTION

Biopharmaceutical drugs, like proteins, are fastidious candidates for the production of a galenic formulation. Because the oral pathway is not accessible for most biopharmaceutical drugs, the formulation must be suitable for parenteral use, which makes aqueous formulations and, for stability reasons, also water-soluble powders the formulation of choice.

Such a formulation needs to fulfil a variety of tasks. It has to be tolerable upon administration, in case of an extravascular administration allow appropriate resorption of the biopharmaceutical into circulation unless the site of action is at the administration location and provide an environment which guarantees stability of the biopharmaceutical drug in a therapeutically effective concentration. Furthermore, the formulation has to enable a shelf life of the drug of at least two years.

Usually, a formulation for a biopharmaceutical drug comprises one or more buffer(s), isotonising agent(s) and water for injection as a solvent. Additionally, stabilisers are frequently added, like for example a cryoprotective agent. Furthermore, one or more metal chelating agent(s) and tenside(s) can be added. Some agents may have a double role, e.g., some sugars or sugar alcohols can serve as a cryoprotective agent and isotonising agent.

An example for an aqueous formulation which is used to formulate a human monoclonal antibody is given in the following table.

| compound | mg | function |
| --- | --- | --- |
| human monoclonal antibody | 40 | active compound |
| sodium chloride | 4.93 | isotonising agent |
| sodiumdihydrogenphosphate × 2 $H_2O$ | 0.69 | buffer |

-continued

| compound | mg | function |
| --- | --- | --- |
| disodiumhydrogenphosphate × 2 $H_2O$ | 1.22 | buffer |
| tri-sodium citrate | 0.24 | buffer |
| citric acid | 1.04 | buffer |
| Mannitol | 9.6 | isotonising agent |
| polysorbate 80 ("Tween 80") | 0.8 | surfactant |
| sodium hydroxide | | pH equilibration |
| Water | ad 0.8 ml | solvent |

An example for a lyophilised formulation, which is used to formulate a chimerised monoclonal antibody, is given in the following table.

| compound | mg per vial | function |
| --- | --- | --- |
| chimeric monoclonal antibody | 100 | active compound |
| sodiumdihydrogenphosphate × 1 $H_2O$ | 2.2 | buffer |
| disodiumhydrogenphosphate × 1 $H_2O$ | 6.1 | cryoprotective |
| Sucrose | 500 | isotonising agent, cryoprotective |
| polysorbate 80 ("Tween 80") | 0.5 | tenside |

Formulations of the above kind meet the requirements set forth above as to tolerability upon administration, stability of the biopharmaceutical drug and shelf life.

However, the said formulations have a number of disadvantages. One disadvantage is that many biopharmaceuticals tend to aggregate, which inevitably alters their physiological properties. In the worst case, such aggregation not only reduces the intended efficacy of the drug, but also increases its immunogenicity, which can lead to serious adverse effects. A favourable formulation would thus contribute to reduce drug aggregation.

Furthermore, some of the ingredients used in current formulations are subject of discussions as to their tolerability. This creates the need to replace the said ingredients.

It is thus the object of the present invention to provide pharmaceutical formulations for biopharmaceutical drugs which can be used as an alternative to those formulations known from prior art.

It is yet another object of the present invention to provide pharmaceutical formulations for biopharmaceutical drugs which are advantageous compared to those formulations known from prior art.

It is yet another object of the present invention to provide pharmaceutical formulations for biopharmaceutical drugs which cause less drug aggregation than those formulations known from prior art.

These objects are met with methods and means according to the independent claims of the present invention. The dependent claims are related to preferred embodiments. It is yet to be understood that value ranges delimited by numerical values are to be understood to include the said delimiting values.

SUMMARY OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an", and "the" include singular and/or plural referents unless the context clearly dictates otherwise. It is moreover to be understood that, in case parameter ranges are given which are delimited by numeric values, the ranges are deemed to include these limitation values.

According to a first aspect of the present invention, a pharmaceutical formulation comprising a biopharmaceutical drug is provided, said formulation further comprising at least one mono- or dicarboxylic acid with a backbone of 2-6 C-Atoms, or at least one salt thereof. The mono- or dicarboxylic acid with a backbone of 2-6 C-Atoms, or its salt, will as well be termed "buffer" in the context of the present invention.

According to the prior art, pharmaceutical formulations are comprising a biopharmaceutical drug, either a non-organic buffer, or salt thereof, like a phosphate buffer, or a tricarboxylic acid, or salt thereof, like citric acid/citrate. The latter is a tricarboxylic acid, which of course provides an efficient buffer function: However, the inventors have found that such buffer may give rise to problems caused by drug aggregation.

In their studies, the inventors surprisingly found that a formulation comprising citric acid (2-hydroxypropan-1,2,3-tricarboxylic acid; $C_6H_8O_7$) or citrate has disadvantages with respect to aggregate formation, in comparison to formulations comprising a mono- or dicarboxylic acid or salt thereof (see results). Citric acid is a branched tricarboxylic acid with a backbone of 5 C-Atoms. Without being bound to any theory, the reason for the poor performance of citric acid might probably be potential chelating effects the three carboxylic groups of such tricarboxylic acid have on charged proteins, like monoclonal antibodies.

The term "2-6 C-Atoms" shall be understood as disclosing all compounds having a backbone of 2, 3, 4, 5, or 6 C-Atoms.

As used herein, the term "biopharmaceutical drug" shall include any therapeutic compound being derived from a biological or from a biotechnological source, or chemically synthesised to be equivalent to a product from said source, for example, a protein, a peptide, a vaccine, a nucleic acid, an immunoglobulin, a polysaccharide, a cell product, a plant extract, an animal extract, a recombinant protein or combinations thereof. Commonly, the biopharmaceutical drug is the active ingredient of a biopharmaceutical.

As used herein, the term "stabiliser" shall refer to an agent which helps to maintain the structural integrity of the biopharmaceutical drug, particularly during freezing and/or lyophilization and/or storage. Such agents are, in the context of the present invention, also called "cryoprotectant" or "lyoprotectant".

As used herein, the term "mono- or dicarboxylic acid with a backbone of n C-Atoms" shall refer to mono- or dicarboxylic acids which have a straight alkyl- or alkylene backbone with n C-Atoms. Said backbone may of course have side chains (e.g. methyl groups); however, the carbon atoms comprised in these chains do not count as C-Atoms of the backbone. According to this definition, cyclic sugar acids, as for example ascorbic acid, do not qualify as "mono- or dicarboxylic acid with a backbone of n C-Atoms", as they do not have a straight alkyl- or alkylene backbone.

In a preferred embodiment of the invention, wherein said formulation is in a form selected from the group consisting of
a) aqueous form
b) lyophilised form, and/or
c) suspension.

In aqueous form, said formulation may be ready for administration, while in lyophilised form said formulation can be transferred into liquid form prior to administration, e.g., by addition of water for injection which may or may not comprise a preservative such as benzyl alcohol, antioxidants like vitamin A, vitamin E, vitamin C, retinyl palmitate, and selenium, the amino acids cysteine and methionine, citric acid and sodium citrate, synthetic preservatives like the parabens methyl paraben and propyl paraben.

In a preferred embodiment of the first aspect of the present invention, said formulation results in reduced aggregation of said biopharmaceutical drug in an aqueous solution, when compared to formulations known from prior art.

As used herein, the term "protein aggregation" shall mean the formation of protein species of higher molecular weight, such as oligomers or multimers, instead of the desired defined species of the biopharmaceutical drug (e.g., a monomer). Protein aggregation is thus a universal term for the formation of all kinds of not further defined multimeric species that are formed by covalent bonds or noncovalent interactions.

In order to determine protein aggregation, poly-dispersity index (PdI) and average protein radius (Z-Ave) can be measured, e.g., by the Dynamic Light Scattering (DLS) method as described below. Aggregates can also be measured by Size Exclusion Chromatography (SE-HPLC or SEC) as described below. Aggregates and particles in general can also be measured by the Microflow Imaging (MFI) method as described below.

Mono- or dicarboxylic acids falling under the above definition are mentioned in the following table:

TABLE 1

| common name | salt | scientific name | net formula |
|---|---|---|---|
| adipic acid | adipate | hexanedioic acid | $C_6H_{10}O_4$ |
| malic acid | malate | hydroxybutanedioic acid | $C_4H_6O_5$ |
| tartaric acid | tartrate | 2,3-dihydroxybutanedioic acid | $C_4H_6O_6$ |
| succinic acid | succinate | butanedioic acid | $C_4H_6O_4$ |
| acetic acid | acetate | ethanoic acid | $C_2H_4O_2$ |
| glutamic acid | glutamate | 2-aminopentanedioic acid | $C_5H_9NO_4$ |
| oxaloacetic acid | oxal acetate | oxobutanedioic acid | $C_4H_4O_5$ |
| glutaric acid | glutarate | pentanedioic acid | $C_5H_8O_4$ |
| α-ketoglutaric acid | α-ketoglutarate | 2-oxopentanedioic acid | $C_5H_6O_5$ |
| maleic acid | maleate | cis-butenedioic acid | $C_4H_4O_4$ |
| fumaric acid | fumarate | trans-butenedioic acid | $C_4H_4O_4$ |

In a particularly preferred embodiment, said mono- or dicarboxylic acid, or salt thereof, is an unbranched dicarboxylic acid (i.e. no C-containing side chains) with a backbone of 4, 5, or 6 C-Atoms, or a salt thereof.

In a particularly preferred embodiment, said mono- or dicarboxylic acid, or salt thereof, is an unbranched monocarboxylic acid with a backbone of 2 C-Atoms, or a salt thereof.

Particularly preferred, said mono- or dicarboxylic acid, or said salt, is at least one selected from the group consisting of:
acetic acid, or acetate
glutamic acid, or glutamate
adipic acid, or adipate
malic acid, or malate
tartaric acid, or tartrate, and/or
succinic acid, or succinate.

Among these, acetic acid, or acetate, is a particularly preferred carboxylic acid or salt. Preferably, it is used as the only carboxylic acid or salt, or even as the only buffer in the pharmaceutical formulation according to the present invention. Adipic acid, or adipate, is another particularly preferred carboxylic acid or salt. Preferably, it is used as the only carboxylic acid or salt, or even as the only buffer in the pharmaceutical formulation according to the present invention.

It is particularly preferred that said mono- or dicarboxylic acid is present in an aqueous form of the pharmaceutical formulation in a concentration of between ≥1 and ≤100 mM, preferably between ≥2 and ≤50 mM, and even more preferably between ≥5 and ≤25 mM.

It is furthermore preferred that, in addition to said mono- or dicarboxylic acid, the pharmaceutical formulation may also contain sodium phosphate (herein also called "NaP") and/or citric acid, or citrate. The term "sodium phosphate" is to be understood as to embrace sodiumdihydrogenphosphate and disodiumhydrogenphosphate, and all conceivable salts and/or hydrates thereof.

Said aqueous form of the pharmaceutical formulation has, preferably, a pH of between ≥3 and ≤9, preferably between ≥4 and ≤8, more preferably between ≥5 and ≤7.

In yet another preferred embodiment, said protein aggregation is induced by shaking agitation, shear stress, multiple freeze-thaw cycles, and/or by long term storage and/or storage at high temperatures.

As used herein, the term "high temperature" shall refer to a storage temperature which is higher than −18° C. Preferably, said high temperature is higher than a temperature selected from the group consisting of 0, 1, 2, 3, 4, 5, 6, 7, 8, 9, 10, 11, 12, 13, 14, 15, 16, 17 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50° C., or even higher. However, one limitation for the storage temperature is the denaturation temperature, which is in the range of 45-80° C., depending on the nature of the respective protein and the medium conditions.

As used herein, the term "long term storage" shall refer to storage of a composition comprising the pharmaceutical formulation for more than 1 month, preferably for more than 2, 3, 4, 5, 6, 7, 8, 9, 10, 11, 12, 13, 14, 15, 16, 17, 18, 19, 20, 21, 22, 23 or even 24 months.

In another preferred embodiment of the present invention, said biopharmaceutical drug is a protein. Said protein can be a naturally occurring protein, a modified protein (i.e., a protein which has been modified with respect to its natural counterpart, also termed scaffold, or template) or a fully synthetic protein (i.e., a protein which has no natural counterpart).

Said protein can either be isolated from a natural organism, or it can be obtained by fermentation of a cultured organism.

Furthermore, said protein can be a protein which is either a homologue or a heterologue to the protein which has been obtained from the organism.

It is particularly preferred that said protein is present in an aqueous form of the pharmaceutical formulation in a concentration of between ≥0.1 and ≤500 mg ml$^{-1}$, preferably between ≥20 and ≤200 mg ml$^{-1}$.

It is particularly preferred that said protein is a monoclonal antibody, or a fragment or derivative thereof.

As used herein, the term "monoclonal antibody (mAb)", shall refer to an antibody composition having a homogenous antibody population, i.e., a homogeneous population consisting of a whole immunoglobulin, or a fragment or derivative thereof. Particularly preferred, such antibody is selected from the group consisting of IgG, IgD, IgE, IgA and/or IgM, or a fragment or derivative thereof.

As used herein, the term "fragment" shall refer to fragments of such antibody retaining, in some cases, target binding capacities, e.g.
  a CDR (complementarity determining region)
  a hypervariable region,
  a variable domain (Fv)
  an IgG heavy chain (consisting of VH, CHL hinge, CH2 and CH3 regions)
  an IgG light chain (consisting of VL and CL regions), and/or
  a Fab and/or F(ab)$_2$.

As used herein, the term "derivative" shall refer to protein constructs being structurally different from, but still having some structural relationship to, the common antibody concept, e.g., scFv, Fab and/or F(ab)$_2$, as well as bi-, tri- or higher specific antibody constructs. All these items are explained below.

Other antibody derivatives known to the skilled person are Diabodies, Camelid Antibodies, Domain Antibodies, bivalent homodimers with two chains consisting of scFvs, IgAs (two IgG structures joined by a J chain and a secretory component), shark antibodies, antibodies consisting of new world primate framework plus non-new world primate CDR, dimerised constructs comprising CH3+VL+VH, and antibody conjugates (e.g. antibody or fragments or derivatives linked to a toxin, a cytokine, a radioisotope or a label).

Methods for the production and/or selection of chimeric, humanised and/or human mAbs are known in the art. For example, U.S. Pat. No. 6,331,415 by Genentech describes the production of chimeric antibodies, while U.S. Pat. No. 6,548,640 by Medical Research Council describes CDR grafting techniques and U.S. Pat. No. 5,859,205 by Celltech describes the production of humanised antibodies. In vitro antibody libraries are, among others, disclosed in U.S. Pat. No. 6,300,064 by MorphoSys and U.S. Pat. No. 6,248,516 by MRC/Scripps/Stratagene. Phage Display techniques are for example disclosed in U.S. Pat. No. 5,223,409 by Dyax. Transgenic mammal platforms are for example described in US200302048621 by TaconicArtemis.

IgG, scFv, Fab and/or F(ab)$_2$ are antibody formats well known to the skilled person. Related enabling techniques are available from the respective textbooks.

As used herein, the term "Fab" relates to an IgG fragment comprising the antigen binding region, said fragment being composed of one constant and one variable domain from each heavy and light chain of the antibody As used herein, the term "F(ab)$_2$" relates to an IgG fragment consisting of two Fab fragments connected to one another by disulfide bonds.

As used herein, the term "scFv" relates to a single-chain variable fragment being a fusion of the variable regions of the heavy and light chains of immunoglobulins, linked together with a short linker, usually serine (S) or glycine (G). This chimeric molecule retains the specificity of the original immunoglobulin, despite removal of the constant regions and the introduction of a linker peptide.

Modified antibody formats are for example bi- or trispecific antibody constructs, antibody-based fusion proteins, immunoconjugates and the like.

In a particularly preferred embodiment of the present invention, said protein is at least one antibody, or fragment or derivative thereof, selected from the group consisting of:
  hybridoma-derived antibody
  chimerised antibody
  humanised antibody, and/or
  human antibody.

In another preferred embodiment of the present invention, said antibody, or fragment or derivative thereof, is an anti-TNFα-antibody.

One example for an anti-TNFα-antibody is defined by the sequence listing enclosed in this application. Therein, SEQ ID No 1 defines the encoding nucleic acid sequence of the IgG heavy chain, SEQ ID No 2 defines the encoding nucleic acid sequence of the IgG light chain, and SEQ ID Nos 3 and 4 define the amino acid sequences of the heavy chain and the light chain, respectively.

SEQ ID Nos 5, 7 and 9 define the amino acid sequences of the complementarity determining regions (CDR) of the light chain (i.e., LC CDR 3, LC CDR 2 and LC CDR 1). SEQ ID Nos 6, 8 and 10 define the amino acid sequences of the complementarity determining regions of the heavy chain (i.e., HC CDR 3, HC CDR 2 and HC CDR 1).

Note that the SEQ ID Nos 1 and 2, or parts thereof, can by equivalently replaced by
- nucleic acid sequences encoding for the same proteins, or the protein chains, encoded by SEQ ID Nos 1 and 2, but have nucleotide substitutions which are tolerable under the degeneracy of the genetic code,
- sequences encoding a fraction, variant, homologue, or derivative of the proteins, or the protein chains, encoded by SEQ ID Nos 1 and 2,
- nucleic acid sequences which are code optimised for a given expression host, and/or
- nucleic acid molecule having a sequence identity of at least 70, preferably 95% with either SEQ ID No 1 or 2

Note that the SEQ ID Nos 3-10, or parts thereof, can by equivalently replaced by amino acid sequences carrying one or more conservative amino acid substitution(s), i.e., one ore more substitution(s) which do not affect significant protein features, like target binding affinity, immunogenicity, ADCC response, serum half life, solubility and so forth.

Other preferred antibodies are antibodies that recognise any one or a combination of proteins including, but not limited to, any of the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1a, IL-1, IL-2, IL-3, IL-7, IL-4, IL-5, IL-8, IL-10, IL-2 receptor, IL-4 receptor, IL-6 receptor, IL-13 receptor, IL-18 receptor subunits, PDGF-β, and analogues thereof, PLGF, VEGF, TGF, TGF-β2, TGF-p1, EGF receptor, PLGF receptor, VEGF receptor, hepatocyte growth factor, osteoprotegerin ligand, interferon gamma, B lymphocyte stimulator, C5 complement, IgE, tumour antigen CA125, tumour antigen MUC1, PEM antigen, ErbB2/HER-2, tumour-associated epitopes that are present in elevated levels in the sera of patients, cancer-associated epitopes or proteins expressed on breast, colon, squamous cell, prostate, pancreatic, lung, and/or kidney cancer cells and/or on melanoma, glioma, or neuroblastoma cells, the necrotic core of a tumour, integrin alpha 4 beta 7, the integrin VLA-4, B2 integrins, TRAIL receptors 1, 2, 3, and 4, RANK, a RANK ligand, TNF-α, the adhesion molecule VAP-1, epithelial cell adhesion molecule (Ep-CAM), intercellular adhesion molecule-3 (ICAM-3), leukointegrin adhesin, the platelet glycoprotein gp IIb/IIIa, cardiac myosin heavy chain, parathyroid hormone, MHC I, carcinoembryonic antigen (CEA), alpha-fetoprotein (AFP), tumour necrosis factor (TNF), Fc-γ-1 receptor, HLA-DR 10 beta, HLA-DR antigen, L-selectin, and IFN-γ.

It is particularly preferred that said antibody is an IgG.

Alternatively, said biopharmaceutical drug is an antibody mimetic, i.e., a non-immunoglobulin-based target-binding protein molecule. Many of the above mentioned techniques are applicable for these molecules as well. Such antibody mimetics are for example derived from Ankyrin Repeat Proteins, C-Type Lectins, A-domain proteins of *Staphylococcus aureus*, Transferrins, Lipocalins, Fibronectins, Kunitz domain protease inhibitors, Ubiquitin, Cysteine knots or knottins, thioredoxin A, and so forth, and are known to the skilled person in the art from the respective literature.

In another alternative, said biopharmaceutical drug is a recombinant fusion protein comprising any of the above-mentioned proteins or substantially similar proteins. For example, recombinant fusion proteins comprising one of the above-mentioned proteins plus a multimerisation domain, such as a leucine zipper, a coiled coil, an Fc portion of an antibody, or a substantially similar protein, can be a biopharmaceutical drug comprised by the formulations of the present invention. Specifically included among such recombinant fusion proteins are proteins in which at least a portion of TNFR or RANK is fused to an Fc portion of an antibody. Particularly preferred, said recombinant fusion proteins comprise a target binding domain and the IgG Fc domain (so-called-cept molecules).

In yet another preferred embodiment of the present invention, the formulation further comprises at least one stabiliser selected from the group consisting of an amino acid, a sugar polyol, a disaccharide and/or a polysaccharide.

Preferably, said disaccharide is an agent selected from the group consisting of sucrose, trehalose, maltose and/or lactose.

Likewise preferably, said sugar polyol is an agent selected from the group consisting of mannitol and/or sorbitol. Among these, mannitol is a particularly preferred sugar polyol. Preferably, it is used as the only sugar polyol, or even the only stabiliser in the pharmaceutical formulation according to the present invention.

Stabilisers falling under the above definition are mentioned in the following table:

TABLE 2

| common name | scientific name | net formula |
|---|---|---|
| arginine | (S)-2-amino-5-guanidinopentanoic acid | $C_6H_{14}N_4O_2$ |
| glycine | aminoacetic acid | $C_2H_5NO_2$ |
| mannitol | (2R,3R,4R,5R)-Hexane-1,2,3,4,5,6-hexol | $C_6H_{14}O_6$ |
| sorbitol | (2S,3R,4R,5R)-Hexane-1,2,3,4,5,6-hexol | $C_6H_{14}O_6$ |
| xylitol | (2R,3R,4S)-Pentane-1,2,3,4,5-pentol | $C_5H_{12}O_5$ |
| sucrose | β-D-fructofuranosyl-(2→1)-α-D-glucopyranoside | $C_{12}H_{22}O_{11}$ |
| trehalose | α-D-glucopyranosyl α-D-glucopyranoside | $C_{12}H_{22}O_{11}$ |
| lactose | 4-O-β-D-galactopyranosyl-D-glucose | $C_{12}H_{22}O_{11}$ |
| maltose | 4-O-α-D-Glucopyranosyl-D-glucose | $C_{12}H_{22}O_{11}$ |
| dextran | polysaccharide | $H(C_6H_{10}O_5)_xOH$ |

It is particularly preferred that said stabiliser is present in an aqueous form of the pharmaceutical formulation in a concentration of between ≥1 mM and ≤300 mM, preferably between ≥2 mM and ≤200 mM, and more preferably between ≥5 mM and ≤150 mM. In yet another preferred embodiment of the present invention, said formulation is a formulation suitable for parenteral administration, preferably for intravenous, intramuscular and/or subcutaneous administration.

In yet another preferred embodiment of the present invention, said formulation further comprises at least one agent selected from the group consisting of:
- a surfactant
- an isotonising agent, and/or
- a metal ion chelator.

Said surfactant enhances the wetability of the components and supports their solubility. This is particularly important because biopharmaceutical drugs are often formulated in high concentrations (e.g., >100 mg in 1-10 ml).

Suitable surfactants are for example lecithin and other non-ionic tensides, like Polysorbates ("TWEEN"), or Poloxameres. Particularly preferred tensides are Polysorbate 80 ("TWEEN 80") or Poloxamere 188.

Said isotonising agent serves for setting the osmotic pressure of the formulation according to the invention to a physiologically acceptable value, e.g. to the osmolarity of blood.

The isotonising agent is an physiologically acceptable component and is not particularly limited. Typical examples of the isotonising agent are, for instance, an inorganic salt such as sodium chloride, potassium chloride or calcium chloride, and the like. These can be used alone or in a mixture thereof.

Said metal ion chelator serves for complex formation of heavy metals, which otherwise may inactivate the biopharmaceutical drug comprised in the formulation according to the invention. Preferably said metal ion chelator is EDTA and/or EGTA.

In a second aspect of the present invention a biopharmaceutical drug is provided, said drug being formulated in a formulation according to the first aspect of the present invention.

In still another (third) aspect of the present invention, a primary packaging, such as a prefilled syringe or pen, a vial, or an infusion bag is provided, which comprises the formulation according to the first aspect of the invention and/or said biopharmaceutical drug according to the second aspect of the present invention.

The prefilled syringe or pen may contain the formulation either in lyophilised form (which has then to be solubilised, e.g., with water for injection, prior to administration), or in aqueous form. Said syringe or pen is often a disposable article for single use only, and may have a volume between 0.1 and 20 ml. However, the syringe or pen may also be a multi-use or multi-dose syringe or pen.

Said vial may also contain the formulation in lyophilised form or in aqueous form, and may serve as a single or multiple use device. As a multiple use device, said vial can have a bigger volume.

Said infusion bag usually contains the formulation in aqueous form and may have a volume between 20 and 5000 ml.

A further (forth) aspect of the invention is the use of a pharmaceutical formulation and/or said biopharmaceutical drug and/or said primary packaging according to the first, second and third aspect, respectively, of the present invention for the treatment of at least one pathologic condition selected from the group consisting of:
- autoimmune diseases
- infectious diseases
- neoplastic and/or malignant diseases (cancer), and/or
- diseases of the nervous system.

Suitable autoimmune diseases are arthritic and rheumatic diseases, like psoriasis, morbus crohn or rheumatoid arthritis. Suitable infectious diseases are viral and/or bacterial infections. Suitable neoplastic and/or malignant diseases are sarcomas, carcinomas, lymphomas and leukaemias, preferably, lung cancer, breast cancer, ovarial cancer, colon cancer, prostate cancer, cervical cancer and the like. Suitable diseases of the nervous system are, among others, neurodegenerative disorders like Parkinson's disease, Alzheimer's disease, multiple sclerosis, Huntington's disease, or Amyotrophic lateral sclerosis.

FIGURES AND EXPERIMENTS

Additional details, features, characteristics and advantages of the object of the invention are disclosed in the subclaims, and the following description of the respective figures and examples, which, in an exemplary fashion, show preferred embodiments of the present invention. However, these drawings should by no means be understood as to limit the scope of the invention.

In the experiments described in the following, formulations according to the present invention underwent particular stress conditions which are suitable to promote aggregation. The experiments are thus relevant to demonstrate an efficient prevention of aggregation as effected by the formulations according to the present invention.

1. BRIEF DESCRIPTION OF THE FIGURES

Figure 1B:
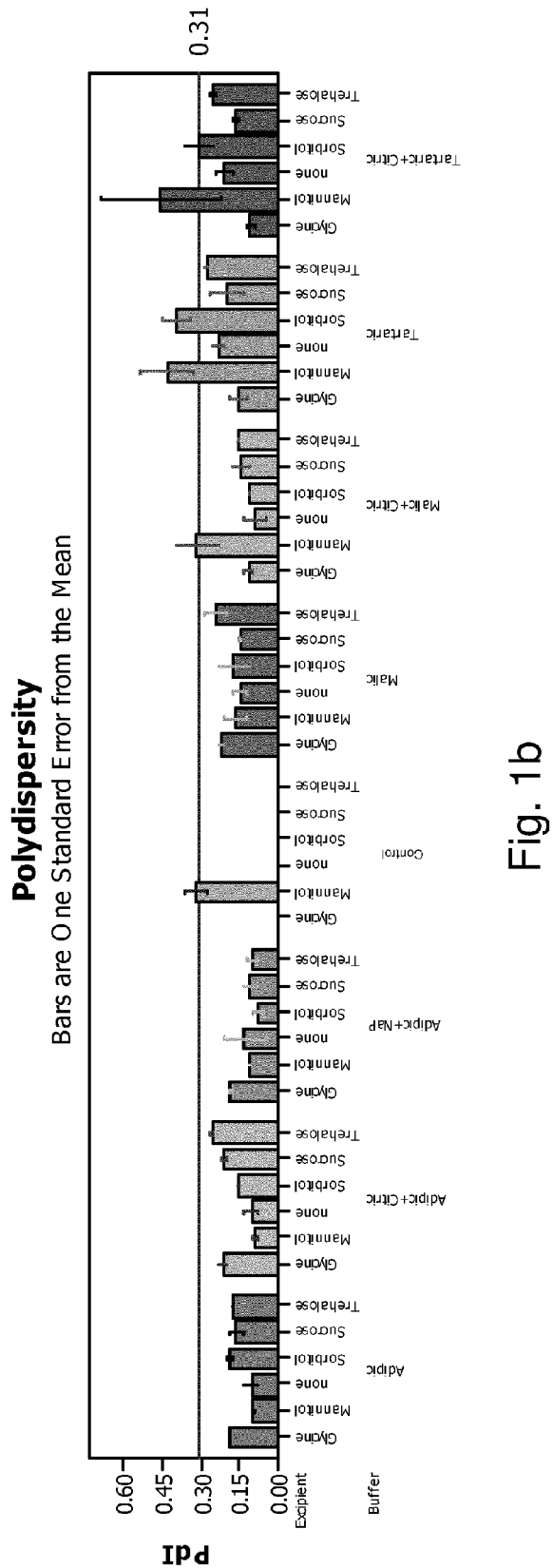

FIG. 1: Shear stress induced aggregation at "stringent" conditions measured by dynamic light scattering (DLS) and expressed as average protein radius, (Z-Ave; FIG. 1a) and poly-dispersity index (PdI; FIG. 1b). The respective average value of the control formulation comprising citric acid and NaP denoted by the horizontal line. The aggregation level is directly proportional to the PdI and increase of the average protein radius (Z-Ave), which means that compositions with a Z-Ave and/or a PdI below the horizontal line exhibit an improved (i.e., reduced) aggregation behaviour than the control formulation. Data underlying the graph in FIG. 1 are shown in Table 6.

Figure 2A:
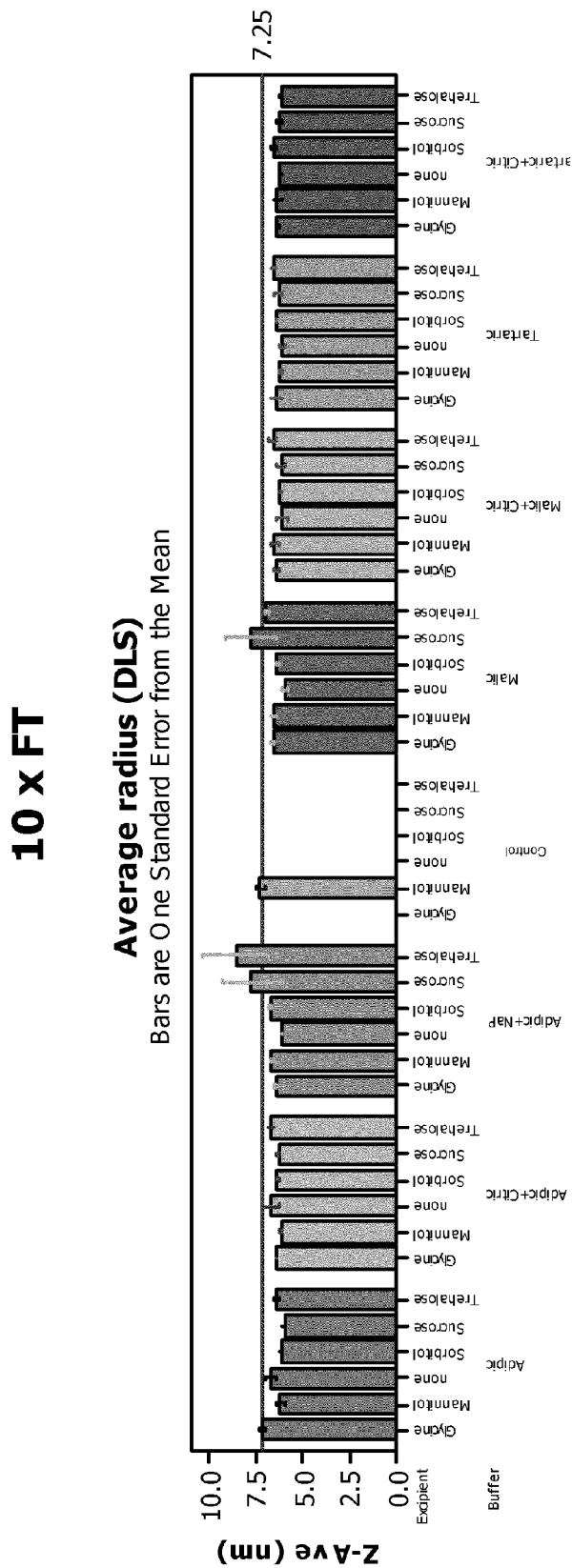
Figure 2B:
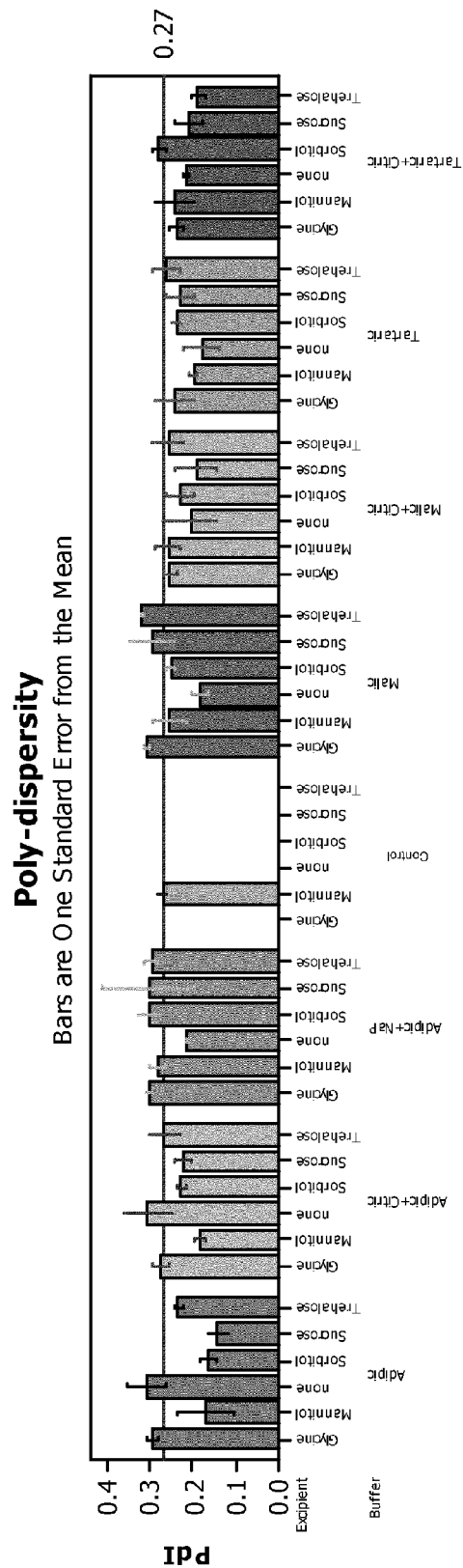

FIG. 2: Freeze-thaw (FT) induced aggregation at "stringent" conditions measured by DLS and expressed as Z-Ave (FIG. 2a) and PdI (FIG. 2b). The respective average value of the control formulation is denoted by the horizontal line. The aggregation level is directly proportional to the PdI and increase of the average protein radius (Z-Ave), which means that compositions with a Z-Ave and/or a PdI below the horizontal line exhibit an improved (i.e., reduced) aggregation behavior than the control formulation. Data underlying the graph in FIG. 2 are shown in Table 6.

Figure 3A:
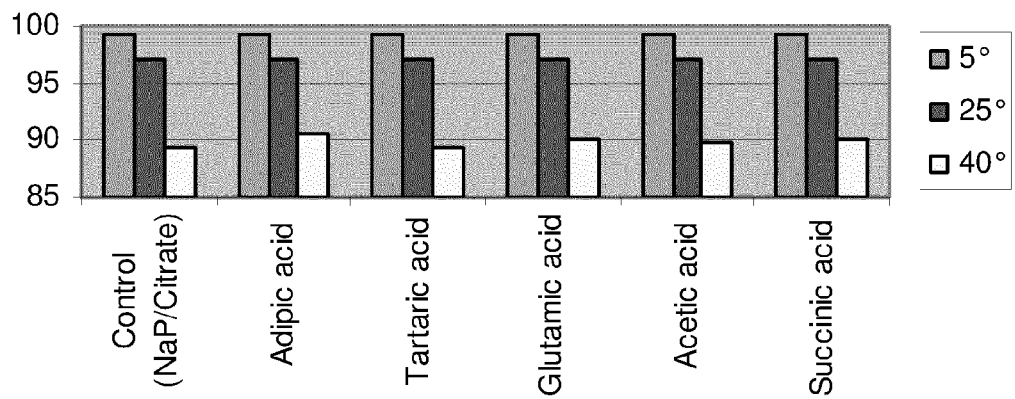
Figure 3B:
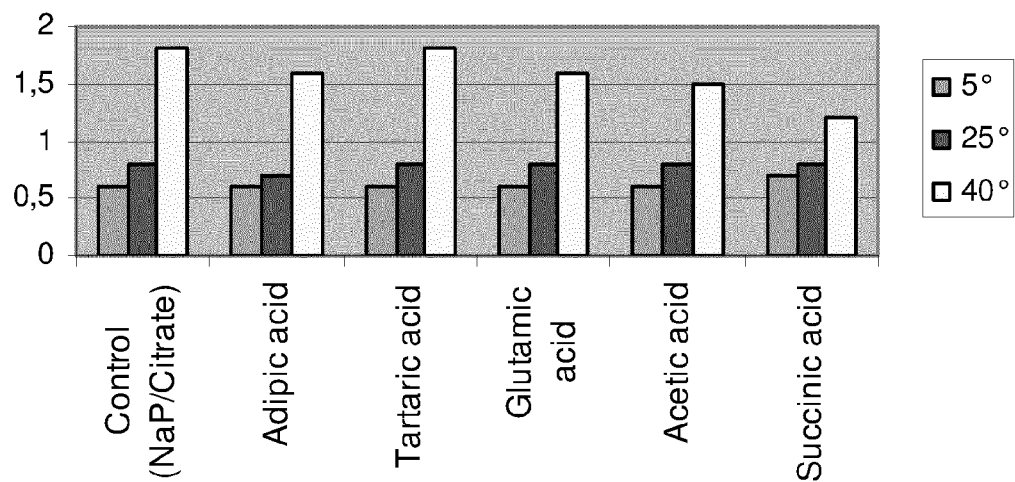

FIG. 3: Stability studies were made with different buffers in formulation containing 105 mM NaCl, 0.1% Tween 80 and 66 mM mannitol, pH was kept at 5.2. Antibody concentration was 50 mg/mL. The samples were stored at different temperatures (5° C., 25° C. and 40° C.) and analysed via Size Exclusion Chromatography to determine purity (FIG. 3a) and aggregate levels (AP=Aggregate Peaks, FIG. 3b). Data underlying the graphs in FIG. 3 are shown in Table 7.

Figure 4A:
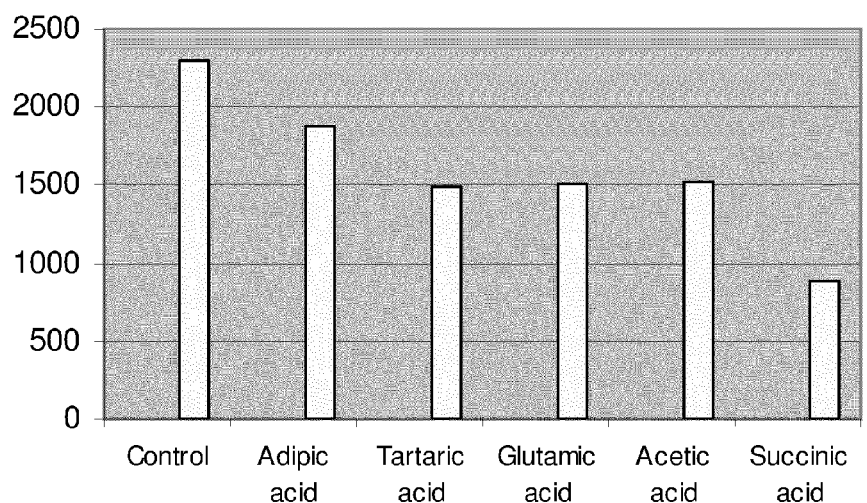
Figure 4B:
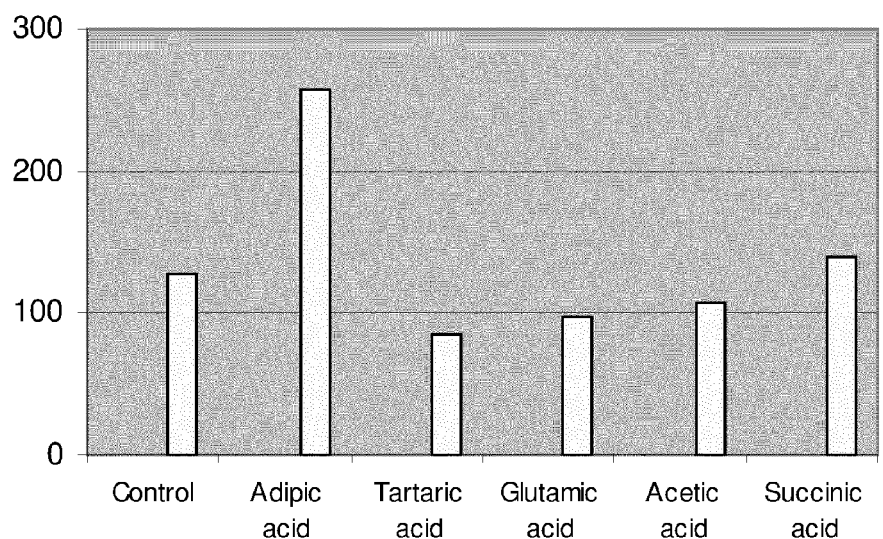

FIG. 4: Further stability studies based on Microflow Imaging (MFI) for detecting subvisible particles were made, with the same conditions as outlined in FIG. 3. Four different trials are shown, with different particle sizes (5-10 µm (FIG. 4a) vs.>10 µm (FIG. 4b)). Data underlying the graphs in FIG. 4 are shown in Table 8.

2. EXPERIMENTS

Before describing the experiments and their results in detail, it is mentioned that the said experiments were made with pharmaceutical formulations in which the active ingredient was an anti-TNF-α antibody (humanised IgG, molecular weight about 150 kD). Due to the structural similarity of antibodies sharing the IgG concept, the skilled person will understand that the results obtained herein can be directly transferred to pharmaceutical formulations comprising murine, rabbit, chimeric, humanised and/or human IgG-based antibodies, and/or to antibodies directed against other targets, e.g., anti-EGFR, anti-ErbB2, anti-CD 20, anti-VEGF and so forth (see list of potential targets above). Further, the skilled person will also acknowledge that this concept can as well be transferred to antibody mimetics, antibody derivatives, modified antibody formats, or recombinant fusion proteins, as defined above.

Further, while some of the buffer/stabiliser combinations which are particularly preferred are disclosed explicitly, and verbally, in the text, the skilled person will acknowledge that in the different figures and tables, specific buffer/stabiliser combinations can be found which perform better, or equally, in comparison to the respective control buffer. These combinations, although not explicitly, and verbally, disclosed in the text, are thus deemed to be unambiguously disclosed as specific combinations, and can therefore serve as fallback positions throughout the prosecution of the present application or respective divisional or continuation application(s).

3. MATERIAL

For the formulation screening, a monoclonal antibody having anti-TNF-α activity was used as an exemplary antibody. The antibody was expressed in a clone derived from the SSF3 cell line (CHO derivative) and purified by protein A affinity chromatography, cation exchange chromatography (CEX) and anion exchange chromatography (AEX) purification steps. The antibody was concentrated to around 50 mg/mL in the desired buffer and stored in aliquots of 1 mL at a temperature below −60° C.

4. FORMULATION PREPARATION FOR SCREENING STUDIES

In the presented study combinations of different carboxylic acids/salts and stabilisers were tested (Tables 3a and 3b, respectively). In some cases a mixture of two different carboxylic acids or a mixture of one carboxylic acid and sodium phosphate (NaP) was used.

Most formulations are according to the invention, i.e., related to a composition comprising at least one mono- or dicarboxylic acid with a backbone of 2-6 C-Atoms, or at least one salt thereof.

Some formulations comprise citric acid and do thus represent the prior art. Herein, these formulations serve as controls and/or comparisons.

All tested formulations contained 105 mM NaCl, 0.1% TWEEN 80 and were formulated at pH around 5.2. Final formulations were prepared from stock solutions. First 988 μL of formulation were prepared by mixing 870 μL of 23 mM acid/salt (Table 3a), 22 μL of 5 M NaCl, 81 μL of 817 M stabiliser (Table 3b) and 15 μL of surfactant 50 mM Tween 80. In one run 42 formulations (7 acid/salt×6 stabilisers) were prepared in a deep well plate. 470 μL of formulation mixture was further transferred into a protein dilution deep well plate, where 30 μL of the antibody at a concentration of about 50 mg/mL was added into even numbered columns and mixed. The targeted protein concentration was thus 3 mg/mL.

Placebo formulations (formulation without protein) were prepared in odd columns, by adding 30 μL of pure water. Finally, 100 μL of each prepared formulation was transferred into four UV transparent half area Greiner Plates (MTP plates). The protein concentration and scattering due to aggregation was assessed immediately after the MTP plate preparation by measuring the A280 and A340/A280 ratio in a Tecan Infinite 200 spectrophotometer. MTP plates were sealed and exposed to appropriate stress assays. Each MTP plate was prepared in duplicate.

In addition to stress stability studies, the effect of the respective formulation composition on the thermodynamic stability of the anti-TNF-α antibody was evaluated. For that purpose the formulations were prepared as described above at a protein concentration of 1 mg/mL.

TABLE 3a

List of tested acids/salts for the experiments in FIGS. 1 and 2 (Table 6). All solutions contained 105 mM NaCl, 0.1% Tween 80 and were formulated at a pH around 5.2.

| buffer formulation No. | acid/salt |
|---|---|
| 1 | 20 mM Glutamate |
| 2 | 20 mM Aconitic Acid |
| 3 | 20 mM Ascorbic Acid |
| 4 | 20 mM Malic Acid |
| 5 | 20 mM Tartaric acid |
| 6 | 20 mM Adipic acid |
| 7 | 20 mM Citric acid |
| 8 | 5 mM Glutamate + 20 mM NaP |
| 9 | 5 mM Malic Acid + 20 mM NaP |
| 10 | 5 mM Tartaric acid + 20 mM NaP |
| 11 | 5 mM Adipic acid + 20 mM NaP |
| 12 | 20 mM Glutamate + 5 mM CitricAcid |
| 13 | 20 mM Malic Acid + 5 mM CitricAcid |
| 14 | 20 mM Tartaric acid + 5 mM CitricAcid |
| 15 | 20 mM Adipic acid + 5 mM CitricAcid |

TABLE 3b

List of stabilisers tested in combinations with the acids/salts of Table 3a.

| stabiliser No. | Stabiliser |
|---|---|
| 1 | Mannitol |
| 2 | Glycine |
| 3 | Trehalose |
| 4 | Sorbitol |
| 5 | Sucrose |
| 6 | None* |

*a set of formulations was prepared without any stabilisers

In one run, 7 organic acids/salts (B1 to B7) and 5 stabilisers (Man=mannitol, Gly=glycine, Thr=trehalose, Sor=sorbitol and Suc=sucrose) were tested. Placebo formulations (without protein, labeled "B") were placed into odd numbered columns, while the formulations containing protein (labeled "P") were placed into even numbered columns.

A commercially available formulation comprising an anti-TNFα antibody in a solution comprising 14.1 mM sodium phosphate, 7.2 mM citrate, 105.5 mM NaCl, 0.1% TWEEN 80 and 65.9 mM mannitol was used as a control formulation (CT=control). The plate design is shown in Table 4.

TABLE 4

Plate design for screening of 42 formulations.

| | 1 | 2 | 3 | 4 | 5 | 6 | 7 | 8 | 9 | 10 | 11 | 12 |
|---|---|---|---|---|---|---|---|---|---|---|---|---|
| A | B1 | P1 | B1 + Man | P1 + Man | B1 + Gly | P1 + Gly | B1 + Thr | P1 + Thr | B1 + Sor | P1 + Sor | B1 + Suc | P1 + Suc |
| B | B2 | P2 | B2 + Man | P2 + Man | B2 + Gly | P2 + Gly | B2 + Thr | P2 + Thr | B2 + Sor | P2 + Sor | B2 + Suc | P2 + Suc |
| C | B3 | P3 | B3 + Man | P3 + Man | B3 + Gly | P3 + Gly | B3 + Thr | P3 + Thr | B3 + Sor | P3 + Sor | B3 + Suc | P3 + Suc |
| D | B4 | P4 | B4 + Man | P4 + Man | B4 + Gly | P4 + Gly | B4 + Thr | P4 + Thr | B4 + Sor | P4 + Sor | B4 + Suc | P4 + Suc |
| E | B5 | P5 | B5 + Man | P5 + Man | B5 + Gly | P5 + Gly | B5 + Thr | P5 + Thr | B5 + Sor | P5 + Sor | B5 + Suc | P5 + Suc |
| F | B6 | P6 | B6 + Man | P6 + Man | B6 + Gly | P6 + Gly | B6 + Thr | P6 + Thr | B6 + Sor | P6 + Sor | B6 + Suc | P6 + Suc |
| G | B7 | P7 | B7 + Man | P7 + Man | B7 + Gly | P7 + Gly | B7 + Thr | P7 + Thr | B7 + Sor | P7 + Sor | B7 + Suc | P7 + Suc |
| H | CT | CT + P | CT | CT + P | CT | CT + P | CT | CT + P | CT | CT + P | CT | CT + P |
| | | B | | B + M | | B + Gly | | B + Thr | | B + Sor | | B + Suc |

5. METHODS

5.1 Stress Assays

The formulation screening was performed by exposing the formulations to two stress assays (freeze/thaw and shaking, respectively) at "mild" and "stringent" conditions. The "mild" conditions are as follows:

3×FT (freezing at −20° C. and thawing at room temperature)
shaking at 400 RPM, 40° C. for 5 days The "stringent" conditions were as follows:

10×FT (freezing at −20° C. and thawing at room temperature)
shaking at 600 RPM, 40° C. for 7 days

5.2 Turbidity (Opalescence)—Absorbance at 340 nm

Clarity or turbidity (opalescence) measurements are based on the fact that incident beams are attenuated due to light scattering. The presence of uniformly suspended particles like insoluble protein aggregates and precipitates leads to an apparent increase in UV absorbance at all wavelengths due to scattering effects. Therefore, the turbidity of formulations was measured as photometric absorbance at 340 nm, where none of the known intrinsic chromophores in the protein formulation absorb, with a Tecan Infinite 200 plate reader.

After 30 s of MTP plate shaking the absorbance at 280 nm, 340 nm, 900 nm and 999 nm was measured. Absorbance A280 and A340 in each well was path-length corrected by multiplying by factor (A999−A900)/0.147. Further, the absorbance of protein solutions was background corrected by subtraction of the respective absorbance of the placebo sample. The protein concentration was thus derived as path-length corrected and background subtracted A280 divided by anti-TNF-α antibody absorbance factor 1.39 and was expressed in mg/mL. The turbidity was expressed as the ratio between background subtracted values A340 and A280.

5.3 Dynamic Light Scattering (DLS)

DLS analysis was performed with the Malvern APS system at a temperature of 25° C. with a semi-conductor laser with a wavelength of 830 nm at a 90° scattering angle. The method is based on measurement of the total scattered light intensity, which is proportional to the protein concentration and molecular size of the scattering particles. The time scale of the scattered light intensity fluctuations was analysed by autocorrelation using the Malvern DLS software. Prior to each measurement, MTP plate was gently shaken to avoid sedimentation of insoluble particles. According to the plate scheduler, 20 μL of the sample were automatically transferred to the measuring cell and returned back to well after measurement. For each measurement, the fluctuation of the scattering intensity was recorded 13 times over a time interval of 5 s to determine the intensity autocorrelation function. By applying multimodal distribution model parameters like the average hydrodynamic protein radius Z-Average (nm), poly-dispersity index PdI, hydrodynamic radius of first three peaks, intensity area of three first peaks, etc. were derived. Non-aggregated protein is described by a mono-disperse size distribution. Protein aggregation results in multiple poly-disperse peaks in size distribution. The aggregation level is traditionally assessed by the increase of the poly-dispersity index (PdI) and increase of the average protein radius (Z-Ave).

5.4 Thermodynamic Stability

Differential scanning calorimetry (DSC) measurements were performed using an Auto Cap-DSC calorimeter from MicroCal, LLC (Northampton, Mass., U.S.A.). For each measurement 400 μL of the sample (formulation containing protein) and reference (placebo formulation) were transferred into a 96-well microtiter plate. The Auto Cap-DSC instrument was run with 15 min equilibration time prior to, and between, the 60° C./h scans. Samples were scanned from 30 to 95° C. with rapid cooling between the scans. DSC data were corrected for instrument baselines and normalised for scan rate and protein concentration. The excess heat capacity (Cp) was expressed in kcal·K$^{-1}$ mol$^{-1}$, wherein 1.000 cal=4.184 J. Data conversion and analysis were performed with the Origin software (OriginLab Corporation, Northampton, Mass., U.S.A.). As it is common for non-reversible thermal transitions of monoclonal antibodies, the stability was assessed by the shifting of the melting temperature of the first peak.

5.5 Micro-Flow Imaging

Micro-Flow Imaging (MFI) is an imaging technology that is used to detect and measure subvisible and visible particulate matter in solutions. The technology captures digital images of particles suspended in a fluid as they pass through a sensing zone, which are automatically analysed to provide a digital archive of particle parameters aspect ratio and intensity. Furthermore, the results are described as the size and count of the particles.

Prior to use the MFI system was purged with 0.9 ml sample buffer. Afterwards 1 ml of sample solution was analysed with the MFI system. The first 0.2 to 0.3 ml was discarded. To evaluate the particle concentration at least 25 images were analysed. After the analysis of 2000 particles the measurement was stopped. The further data evaluation was performed with MFI application software. Samples can be analysed regarding size distribution or with shape analysis to get further information e.g. aspect ratio.

5.6 Size Exclusion Chromatography

Size exclusion chromatography (SE-HPLC or SEC) was used to separate lower and higher molecular mass variants of the protein as well as any impurities and formulation ingredients.

The results were described as the summation of aggregation peaks (APs) and summation of degradation peaks (DPs). In SEC, the identity of test samples was determined by comparing the chromatographic retention time of the major peaks with the retention time of the major peak of a reference standard.

SEC was performed using one Tosoh Bioscience TSK-Gel G3000SWXL columns (5 μm, 250 Å, 7.8 mm I.D.×300 mm length) (Tosoh Bioscience, Stuttgart, Germany) and a mobile phase containing 150 mM potassium phosphate, pH 6.5. The flow rate was set to 0.4 ml/min and the column temperature to 30° C. Samples were diluted with mobile phase to a concentration of 0.75 mg/ml and injection volume was 10 μl.

6. CONFIRMATION STUDIES

To confirm the results obtained by the formulation screening studies described above, a stability study was set up. The antibody was prepared as specified above and additionally dialysed into different butler systems. The formulations prepared contained 105 mM NaCl, 0.1% TWEEN 80 and 66 mM mannitol, pH was kept at 5.2. Antibody concentration was 50 mg/mL. The samples were stored at different temperatures (5° C., 25° C. and 40° C.) and analysed Via Size Exclusion Chromatography (SE-HPLC) to determine purity and aggregate levels as well as Microflow Imaging (MFI) for detecting subvisible particles. While, with SE-HPLC, particularly dimeric, trimeric, tetrameric and pentameric aggregates of the respective antibody can be detected (i.e., aggregates with a molecular weight of up to 800 kD), Microflow Imaging (MFI) serves to detect subvisible particles in a size range of 5-30 μm, i.e., about 1000× bigger aggregates then those detectable by SE-HPLC.

7. RESULTS

In order to identify formulation compositions that protect the anti-TNF-α antibody from aggregation at the same level as the control formulation various different formulations (Table 3) were screened in two rounds. In a first round the formulations containing anti-TNF-α antibody were exposed to two stress assays at "mild" conditions (3×FT) and shaking at 400 RPM, 40° C. for 5 days. After the first stress experiment, the aggregation level in each sample was determined by measuring size distribution using DLS.

In addition to the assessment of the aggregation protection potential, the effect of the screened formulations on the thermodynamic stability of the anti-TNF-α antibody was measured in order to further show the suitability of the inventive formulations to maintain the structural integrity of the biopharmaceutical drug stored therein. DSC thermograms were scanned from 30-90° C. The melting temperatures (Tm; temperature of the first peak) of the anti-TNF-α antibody within the screened formulations according to the invention were in the range of about 70° C. to about 72° C. which is comparable to the respective melting temperature within the control formulation ($T_m$=71.46±0.06° C. (N=11)). Detailed Tm values are given in Table 5. In Table 5, formulations comprising only the tricarboxylic acids aconitic acid or citric acid as carboxylic acid/salt serve as controls, and are printed in italics and marked with an asterisk (*).

Based on the DLS and DSC data obtained with the "mild" condition screening the following formulations containing Adipic, Adipic+Citric, Adipic+NaP, Malic, Malic+Citric, Tartaric or Tartaric+Citric in combination with and without stabiliser (Glycine, Mannitol, Sorbitol, Sucrose or Trehalose), respectively, were selected for further evaluation, this time under "stringent" conditions.

The selection was based on their similarity of PdI, Z-Ave and Tm as compared to the respective values of the control formulation (indicating upfront their suitability for human medical use). To detect any superior behaviour of the tested formulations in comparison to the control formulation the samples were further screened at "stringent" conditions (10×FT and shaking at 600 RPM, 40° C. for 7 days). Experiments were performed in duplicates.

Induced aggregation was detected by DLS (Table 6, FIGS. 1 and 2). Turbidity measurements did not show any aggregation. Surprisingly, the aggregation was significantly more pronounced for anti-TNF-α antibody formulated in the control formulation (FIGS. 1 and 2) than in formulations according to the invention, e.g., comprising a mono- or dicarboxylic acid.

The aggregation assessed by Z-Ave (FIG. 1a) and PdI (FIG. 1b) after 600 RPM shaking for 7 days at 40° C. showed that all buffer/stabiliser combinations according to the invention (e.g. adipic acid+mannitol) demonstrated a better performance, i.e., a smaller Z-Ave or PdI, than the control buffer (citric acid/NaP+mannitol), with the exception of some combinations comprising tartaric acid (Z-Ave: tartaric acid+mannitol or sorbitol; tartaric acid/citric acid+mannitol or sorbitol or trehalose; PdI: tartaric acid+mannitol or sorbitol; tartaric acid/citric acid+mannitol or sorbitol).

Note that resulting standard deviations indicated by the error bars are usually quite small, thus indicating the statistical significance of the performance difference between the control (Z-Ave value or PdI of which is indicated by the horizontal bar, i.e., 9.58 nm, or 0.31) and the respective buffer. In contrast thereto, for the combinations comprising tartaric acid which perform worse than the control buffer large standard deviations have been observed, which indicates that the respective experiments might have been subject to particular artifacts.

As regards the freeze/thaw experiments, results are shown in FIGS. 2a and 2b. These experiments show that under the respective conditions all tested formulations demonstrate a similar behaviour (indicated by large error bars in the PdI experiment in FIG. 2b), while some claimed formulations (e.g. adipic acid+mannitol, sorbitol or sucrose) perform significantly better than the control formulation.

Results of the confirmation studies in which different buffers were formulated in solution comprising mannitol (see above) are shown in tables 8 and 9, and FIGS. 3 and 4. Size exclusion chromatography (SE-HPLC) experiments after 3 months stability study at 5, 25 and 40° C. (Table 7) revealed that, due to aggregation and degradation of the active compound (anti-TNF-α antibody), purity decreased to something between about 98% (storage at 5° C.) and 87% (storage at 40° C.). In this experiment, all compared buffers performed in a similar manner. See FIG. 3a for graphic representation. Initial purity at the beginning of the experiments was between 99.2 and 93% for all tested formulations.

However, the sum of aggregation peaks also detected with SE-HPLC were, for phosphate/citrate buffer (control) significantly higher (1.8% at 40° C. storage) than for most of the buffers claimed according to the invention, e.g., 1.2% (succinic acid) or 1.5% (acetic acid). See FIG. 3b for graphic representation.

Microflow Imaging (MFI) experiments, in which particles of a given size range were counted in a given sample volume, served to detect the formation of macroaggregations in the range of 5-30 μm after 3 months storage at 40° C. It is evident that in the size range of 5-10 μm, all claimed buffers performed better than the control buffer (i.e., citric acid+NaP). See FIG. 4a for graphic representation. Adipic acid+mannitol and acetic acid+mannitol perform particularly well under these conditions.

In the size range of >10 μm, all buffers perform in such way that the number of particles ml$^{-1}$ is below 260, which is about 30× below the respective limits set forth by the European Pharmacopoeia (6.0), according to which particulate contamination of injections and infusions is restricted to 7500 particles ml$^{-1}$ for particles>10 μm. See FIG. 4a for a graphic representation. Due to the good performance of all buffers the particle count was very small, which means that, statistically, the results are subject to large relative standard deviations due to small particle counts, suggesting that the apparent differences in mean particle count are not significant, e.g., between control and adipic acid.

TABLE 5

Effect of acid/salt composition and stabiliser on melting temperature measured by DSC

|    | Acid/salt | Stabiliser | Tm(° C.) |
|----|-----------|------------|----------|
| 1  | Control (sodium phosphate + citrate) | Mannitol | 71.45 |
| 2  | Aconitic* | Mannitol | 70.47 |
| 3  | Aconitic* | None | 70.04 |
| 4  | Adipic | Glycine | 71.03 |
| 5  | Adipic | Mannitol | 70.95 |
| 6  | Adipic | None | 70.8 |
| 7  | Adipic | Sorbitol | 71.06 |
| 8  | Adipic | Sucrose | 71.1 |
| 9  | Adipic | Trehalose | 71.02 |
| 10 | Adipic Citric | Glycine | 71.21 |
| 11 | Adipic Citric | Mannitol | 70.96 |
| 12 | Adipic Citric | Sorbitol | 71.12 |
| 13 | Adipic Citric | Sucrose | 71.24 |
| 14 | Adipic Citric | Trehalose | 71.23 |
| 15 | Adipic NaP | Glycine | 71.47 |
| 16 | Adipic NaP | Mannitol | 71.56 |
| 17 | Adipic NaP | Sorbitol | 71.49 |
| 18 | Adipic NaP | Sucrose | 71.58 |
| 19 | Adipic NaP | Trehalose | 71.74 |
| 20 | Ascorbic | Mannitol | 70.94 |
| 21 | Ascorbic | None | 70.56 |
| 22 | Citric* | Mannitol | 70.53 |
| 23 | Citric* | None | 70.49 |
| 24 | Glutamic | Glycine | 71.92 |
| 25 | Glutamic | Mannitol | 71.51 |
| 26 | Glutamic | None | 70.89 |
| 27 | Glutamic | Sorbitol | 71.92 |
| 28 | Glutamic | Sucrose | 71.82 |
| 29 | Glutamic | Trehalose | 71.91 |
| 30 | Glutamic Citric | Glycine | 71.88 |
| 31 | Glutamic Citric | Mannitol | 71.86 |
| 32 | Glutamic Citric | Sorbitol | 71.88 |
| 33 | Glutamic Citric | Sucrose | 71.9 |
| 34 | Glutamic Citric | Trehalose | 71.9 |
| 35 | Glutamic NaP | Glycine | 71.82 |
| 36 | Glutamic NaP | Mannitol | 71.76 |
| 37 | Glutamic NaP | Sorbitol | 71.71 |
| 38 | Glutamic NaP | Sucrose | 72.01 |
| 39 | Glutamic NaP | Trehalose | 71.9 |
| 40 | Malic | Glycine | 71.19 |
| 41 | Malic | Mannitol | 70.79 |
| 42 | Malic | None | 70.99 |
| 43 | Malic | Sorbitol | 71.19 |
| 44 | Malic | Sucrose | 71.19 |
| 45 | Malic | Trehalose | 71.31 |
| 46 | Malic Citric | Glycine | 71.38 |
| 47 | Malic Citric | Mannitol | 71.28 |
| 48 | Malic Citric | Sorbitol | 71.33 |
| 49 | Malic Citric | Sucrose | 71.4 |
| 50 | Malic Citric | Trehalose | 71.4 |
| 51 | Malic NaP | Glycine | 71.41 |
| 52 | Malic NaP | Mannitol | 71.66 |
| 53 | Malic NaP | Sorbitol | 71.8 |
| 54 | Malic NaP | Sucrose | 71.98 |
| 55 | Malic NaP | Trehalose | 71.73 |
| 56 | NaP | Mannitol | 71.28 |
| 57 | NaP | None | 70.89 |
| 58 | Tartaric | Glycine | 71.4 |
| 59 | Tartaric | Mannitol | 71.1 |
| 60 | Tartaric | None | 70.94 |
| 61 | Tartaric | Sorbitol | 71.46 |
| 62 | Tartaric | Sucrose | 71.29 |
| 63 | Tartaric | Trehalose | 71.28 |
| 64 | Tartaric Citric | Glycine | 71.71 |
| 65 | Tartaric Citric | Mannitol | 71.45 |
| 66 | Tartaric Citric | Sorbitol | 71.53 |
| 67 | Tartaric Citric | Sucrose | 71.74 |
| 68 | Tartaric Citric | Trehalose | 71.72 |
| 69 | Tartaric NaP | Glycine | 71.6 |
| 70 | Tartaric NaP | Mannitol | 71.65 |
| 71 | Tartaric NaP | Sorbitol | 71.77 |
| 72 | Tartaric NaP | Sucrose | 71.92 |
| 73 | Tartaric NaP | Trehalose | 71.91 |

TABLE 6

Shear stress or freeze/thaw induced aggregation at "stringent" conditions measured by DLS (PdI-poly dispersity, Z-Ave - average radius, N = 2, except for the control formulation, where N = 12)

| | | 10 x FT | | | | 600 RPM shaking 7 days 40° C. | | | |
| | | Z-Ave (nm) | | PdI | | Z-Ave (nm) | | PdI | |
| Acid/Salt | Stabiliser | Mean | StDev | Mean | StDev | Mean | StDev | Mean | StDev |
|---|---|---|---|---|---|---|---|---|---|
| Control (sodium phosphate + citrate) | Mannitol | 7.26 | 0.96 | 0.27 | 0.04 | 9.58 | 3.87 | 0.31 | 0.15 |
| Adipic | Glycine | 7.13 | 0.25 | 0.29 | 0.02 | 6.00 | 0.17 | 0.18 | 0.01 |
| Adipic | Mannitol | 6.22 | 0.32 | 0.17 | 0.09 | 5.82 | 0.12 | 0.09 | 0.01 |

TABLE 6-continued

Shear stress or freeze/thaw induced aggregation at "stringent" conditions measured by DLS (PdI-poly dispersity, Z-Ave - average radius, N = 2, except for the control formulation, where N = 12)

|  |  | 10 x FT | | | | 600 RPM shaking 7 days 40° C. | | | |
| --- | --- | --- | --- | --- | --- | --- | --- | --- | --- |
|  |  | Z-Ave (nm) | | PdI | | Z-Ave (nm) | | PdI | |
| Acid/Salt | Stabiliser | Mean | StDev | Mean | StDev | Mean | StDev | Mean | StDev |
| Adipic | None | 6.74 | 0.40 | 0.31 | 0.06 | 5.85 | 0.17 | 0.10 | 0.04 |
| Adipic | Sorbitol | 6.12 | 0.09 | 0.17 | 0.03 | 6.09 | 0.02 | 0.19 | 0.02 |
| Adipic | Sucrose | 5.98 | 0.17 | 0.14 | 0.03 | 6.06 | 0.23 | 0.16 | 0.04 |
| Adipic | Trehalose | 6.37 | 0.22 | 0.23 | 0.01 | 7.61 | 2.33 | 0.17 | 0.00 |
| Adipic + Citric | Glycine | 6.37 | 0.02 | 0.27 | 0.03 | 6.03 | 0.01 | 0.21 | 0.02 |
| Adipic + Citric | Mannitol | 6.14 | 0.07 | 0.18 | 0.02 | 5.87 | 0.13 | 0.09 | 0.02 |
| Adipic + Citric | None | 6.69 | 0.59 | 0.30 | 0.08 | 5.88 | 0.09 | 0.10 | 0.04 |
| Adipic + Citric | Sorbitol | 6.35 | 0.07 | 0.22 | 0.02 | 5.99 | 0.13 | 0.15 | 0.00 |
| Adipic + Citric | Sucrose | 6.27 | 0.08 | 0.22 | 0.02 | 6.23 | 0.02 | 0.21 | 0.01 |
| Adipic + Citric | Trehalose | 6.67 | 0.25 | 0.26 | 0.05 | 6.51 | 0.06 | 0.25 | 0.00 |
| Adipic + NaP | Glycine | 6.44 | 0.06 | 0.30 | 0.01 | 5.95 | 0.11 | 0.18 | 0.01 |
| Adipic + NaP | Mannitol | 6.63 | 0.13 | 0.28 | 0.03 | 6.02 | 0.21 | 0.11 | 0.00 |
| Adipic + NaP | None | 6.07 | 0.01 | 0.21 | 0.00 | 6.01 | 0.48 | 0.13 | 0.11 |
| Adipic + NaP | Sorbitol | 6.74 | 0.15 | 0.30 | 0.04 | 5.80 | 0.20 | 0.08 | 0.03 |
| Adipic + NaP | Sucrose | 7.72 | 2.26 | 0.30 | 0.15 | 5.85 | 0.20 | 0.10 | 0.04 |
| Adipic + NaP | Trehalose | 8.59 | 2.47 | 0.30 | 0.02 | 5.81 | 0.04 | 0.10 | 0.03 |
| Malic | Glycine | 6.60 | 0.07 | 0.31 | 0.01 | 6.05 | 0.24 | 0.22 | 0.01 |
| Malic | Mannitol | 6.48 | 0.21 | 0.26 | 0.06 | 6.16 | 0.24 | 0.17 | 0.06 |
| Malic | None | 5.95 | 0.16 | 0.18 | 0.03 | 5.90 | 0.19 | 0.15 | 0.04 |
| Malic | Sorbitol | 6.36 | 0.08 | 0.25 | 0.01 | 6.10 | 0.33 | 0.17 | 0.08 |
| Malic | Sucrose | 7.74 | 1.99 | 0.29 | 0.07 | 6.82 | 1.21 | 0.15 | 0.01 |
| Malic | Trehalose | 6.93 | 0.02 | 0.32 | 0.00 | 6.20 | 0.19 | 0.24 | 0.06 |
| Malic + Citric | Glycine | 6.35 | 0.18 | 0.25 | 0.02 | 5.79 | 0.08 | 0.11 | 0.02 |
| Malic + Citric | Mannitol | 6.49 | 0.28 | 0.26 | 0.04 | 7.68 | 1.72 | 0.31 | 0.12 |
| Malic + Citric | None | 6.12 | 0.38 | 0.20 | 0.09 | 5.75 | 0.23 | 0.09 | 0.06 |
| Malic + Citric | Sorbitol | 6.19 | 0.14 | 0.23 | 0.05 | 5.91 | 0.01 | 0.11 | 0.00 |
| Malic + Citric | Sucrose | 6.16 | 0.33 | 0.19 | 0.07 | 5.94 | 0.01 | 0.14 | 0.05 |
| Malic + Citric | Trehalose | 6.61 | 0.25 | 0.26 | 0.05 | 8.14 | 3.05 | 0.16 | 0.00 |
| Tartaric | Glycine | 6.39 | 0.46 | 0.24 | 0.06 | 5.95 | 0.16 | 0.15 | 0.04 |
| Tartaric | Mannitol | 6.20 | 0.09 | 0.20 | 0.01 | 24.62 | 20.25 | 0.43 | 0.14 |
| Tartaric | None | 6.05 | 0.18 | 0.18 | 0.06 | 6.27 | 0.47 | 0.23 | 0.03 |
| Tartaric | Sorbitol | 6.39 | 0.08 | 0.24 | 0.01 | 32.57 | 12.48 | 0.39 | 0.08 |
| Tartaric | Sucrose | 6.29 | 0.32 | 0.23 | 0.05 | 8.22 | 2.79 | 0.20 | 0.10 |
| Tartaric | Trehalose | 6.55 | 0.25 | 0.26 | 0.05 | 6.57 | 0.01 | 0.27 | 0.01 |
| Tartaric + Citric | Glycine | 6.32 | 0.19 | 0.24 | 0.03 | 5.86 | 0.03 | 0.11 | 0.02 |
| Tartaric + Citric | Mannitol | 6.36 | 0.31 | 0.24 | 0.06 | 12.89 | 0.96 | 0.45 | 0.33 |
| Tartaric + Citric | None | 6.17 | 0.07 | 0.22 | 0.01 | 6.71 | 1.18 | 0.20 | 0.04 |
| Tartaric + Citric | Sorbitol | 6.53 | 0.18 | 0.28 | 0.02 | 12.41 | 6.32 | 0.31 | 0.08 |
| Tartaric + Citric | Sucrose | 6.22 | 0.16 | 0.21 | 0.05 | 5.98 | 0.10 | 0.16 | 0.01 |
| Tartaric + Citric | Trehalose | 6.12 | 0.13 | 0.19 | 0.02 | 13.61 | 10.30 | 0.25 | 0.01 |

TABLE 7

Stability study, SE-HPLC results - purity and sum of aggregation peaks (AP)

| Buffer | Control (NaP/Citrate) | Adipic acid | Tartaric acid | Glutamic acid | Acetic acid | Succinic acid |
| --- | --- | --- | --- | --- | --- | --- |
| Test parameter | Purity and Related substances by SE-HPLC - Purity - in [Area-%] | | | | | |
| Temp. | 5° C. | 5° C. | 5° C. | 5° C. | 5° C. | 5° C. |
| initial | 99.3 | 99.2 | 99.3 | 99.3 | 99.3 | 99.2 |
| 6 weeks | 99.2 | 99.2 | 99.2 | 99.0 | 99.1 | 99.0 |
| 3 months | 99.2 | 99.3 | 99.2 | 99.3 | 99.3 | 99.2 |
| Temp. | 25° C. | 25° C. | 25° C. | 25° C. | 25° C. | 25° C. |
| initial | 99.3 | 99.2 | 99.3 | 99.3 | 99.3 | 99.2 |
| 6 weeks | 97.7 | 97.7 | 97.7 | 97.8 | 97.8 | 97.8 |
| 3 months | 97.1 | 97.2 | 97.1 | 97.2 | 97.2 | 97.1 |

TABLE 7-continued

Stability study, SE-HPLC results - purity and sum of aggregation peaks (AP)

| Buffer | Control (NaP/Citrate) | Adipic acid | Tartaric acid | Glutamic acid | Acetic acid | Succinic acid |
|---|---|---|---|---|---|---|
| Temp. | 40° C. | 40° C. | 40° C. | 40° C. | 40° C. | 40° C. |
| initial | 99.3 | 99.2 | 99.3 | 99.3 | 99.3 | 99.2 |
| 3 weeks | 95.9 | 96.2 | 95.7 | 96.0 | 95.9 | 95.9 |
| 6 weeks | 93.6 | 94.3 | 93.5 | 93.9 | 93.7 | 93.8 |
| 3 months | 89.4 | 90.5 | 89.3 | 90.0 | 89.9 | 90.0 |
| Test parameter | \multicolumn{6}{l}{Purity and Related substances by SE-HPLC - Sum of AP's - soluble aggregates detected by SEC - in [Area-%]} | | | | | |
| Temp. | 5° C. | 5° C. | 5° C. | 5° C. | 5° C. | 5° C. |
| initial | 0.7 | 0.7 | 0.7 | 0.7 | 0.7 | 0.7 |
| 6 weeks | 0.6 | 0.6 | 0.6 | 0.7 | 0.5 | 0.5 |
| 3 months | 0.6 | 0.6 | 0.6 | 0.6 | 0.6 | 0.7 |
| Temp. | 25° C. | 25° C. | 25° C. | 25° C. | 25° C. | 25° C. |
| initial | 0.7 | 0.7 | 0.7 | 0.7 | 0.7 | 0.7 |
| 6 weeks | 0.9 | 0.9 | 0.9 | 0.9 | 0.9 | 0.9 |
| 3 months | 0.8 | 0.7 | 0.8 | 0.8 | 0.8 | 0.8 |
| Temp. | 40° C. | 40° C. | 40° C. | 40° C. | 40° C. | 40° C. |
| initial | 0.7 | 0.7 | 0.7 | 0.7 | 0.7 | 0.7 |
| 3 weeks | 1.0 | 0.9 | 0.9 | 0.9 | 1.0 | 0.9 |
| Test parameter | \multicolumn{6}{l}{Purity and Related substances by SE-HPLC - Purity - in [Area-%]} | | | | | |
| 6 weeks | 1.5 | 1.4 | 1.5 | 1.4 | 1.6 | 1.5 |
| 3 months | 1.8 | 1.6 | 1.8 | 1.6 | 1.5 | 1.2 |

TABLE 8

Stability study, MFI results—Total amount of particles 5-10 μm and >10 μm Data taken after 3 months storage at 40° C.

| Control (NaP/Citrate) | Adipic acid | Tartaric acid | Glutamic acid | Acetic acid | Succinic acid |
|---|---|---|---|---|---|
| \multicolumn{6}{l}{Sub-visible particles by Flow Microscopy (Micro Flow Imaging, MFI)—5-10 μm-in [counts/mL} | | | | | |
| 2296 | 1874 | 1483 | 1507 | 1520 | 881 |
| \multicolumn{6}{l}{Sub-visible particles by Flow Microscopy (Micro Flow Imaging, MFI)— larger than 10 μm-in [counts/mL]} | | | | | |
| 127 | 257 | 86 | 98 | 107 | 139 |

TABLE 9

Two examples for a preferred formulation according to the invention

| compound | [mg/mL] |
|---|---|
| chimeric, humanised or human IgG | 50.00 |
| NaCl | 5.0-7.0 |
| Mannitol | 10.0-14.0 |
| Adipic acid | 1.5-4.0 |
| Tween 80 | 0.5-1.5 |

TABLE 9-continued

Two examples for a preferred formulation according to the invention

| compound | [mg/mL] |
|---|---|
| NaOH (to adjust pH) | q.s. |
| pH | 5.20 |
| chimeric, humanised human IgG | 50.00 |
| NaCl | 5.0-7.0 |
| Mannitol | 10.0-14.0 |
| Acetic acid | 0,.5-1.5 |
| Tween 80 | 0.5-1.5 |
| NaOH (to adjust pH) | q.s. |
| pH | 5.20 |

Table 10 shows particularly preferred formulations comprising adipic acid or acetic acid (acetate). These formulations were compared with the control buffer comprising sodium phosphate+citrate (14.1 mM sodium phosphate, 7.2 mM citrate, 105.5 mM NaCl, 0.1% Tween 80 and 65.9 mM mannitol, see further details above). All shown formulations were superior over the control buffer in terms of aggregation behaviour.

TABLE 10

Preferred formulations comprising adipic acid or acetate.

| | 001 | | 007 | | |
| --- | --- | --- | --- | --- | --- |
| Study No | Adipic acid formulation | Acetic acid formulation | Adipic acid formulation | Adipic/ Citrate formulation | Acetic acid formulation |
| NaCl [mM] | 105 | 105 | 105 | 105 | 105 |
| Mannitol [mM] | 66 | 66 | 66 | 66 | 66 |
| Adipic acid [mM] | 23 | — | 23 | 23 | <0.2 |
| Acetic acid [mM] | — | 20 | — | — | 20 |
| Tween 80 [mM] | 0.8 | 0.8 | 0.8 | 0.8 | 0.8 |
| Citric acid [mM] | 1.4 | 2.4 | — | 1.4 | 2.4 |
| Phosphate [mM] | 2.8 | 2.8 | — | — | — |

What is claimed is:

1. A pharmaceutical formulation comprising a biopharmaceutical drug, said composition further comprising
   adipic acid, or adipate,
   wherein said biopharmaceutical drug is an anti-tumor necrosis factor alpha (TNFα) antibody or an antigen binding fragment thereof.

2. The formulation according to claim 1, which formulation further comprises at least one stabiliser selected from the group consisting of an amino acid, a sugar polyol, a disaccharide and a polysaccharide.

3. The formulation according to claim 2, wherein said disaccharide is an agent selected from the group consisting of sucrose and trehalose.

4. The formulation according to claim 2, wherein said sugar polyol is an agent selected from the group consisting of mannitol and sorbitol.

5. The formulation according to claim 1, wherein said formulation results in reduced aggregation of said biopharmaceutical drug in an aqueous solution.

6. The formulation according to claim 1, wherein said antibody, or antigen binding fragment thereof, is selected from the group consisting of: hybridoma-derived antibody, chimerised antibody, monoclonal antibody, humanised antibody, and human antibody.

7. The formulation according to claim 1, wherein said antibody is an IgG.

8. The formulation according to claim 1, wherein said antibody is a human antibody.

9. A prefilled syringe or pen, a vial or an infusion bag, said syringe or pen, vial or infusion bag comprising a formulation according to claim 1.

10. A treatment method comprising administering an effective amount of a pharmaceutical formulation comprising a biopharmaceutical drug to a subject with a pathologic condition, said composition further comprising adipic acid or adipate,
  wherein said biopharmaceutical drug is an anti-tumor necrosis factor alpha (TNFα) antibody or antigen binding fragment thereof, and wherein the pathologic condition is an autoimmune disease.

* * * * *